United States Patent [19]

Lassmann et al.

[11] 4,081,257
[45] Mar. 28, 1978

[54] FREEZE REGENERATION OF GLYCOL SOLUTIONS LOADED WITH WATER

[75] Inventors: Eberhard Lassmann, Herrnhausen; Heinz Karwat, Pullach, both of Germany

[73] Assignee: Linde Aktiengesellschaft, Wiesbaden, Germany

[21] Appl. No.: 671,991

[22] Filed: Mar. 30, 1976

[30] Foreign Application Priority Data

Apr. 1, 1975 Germany .............................. 2514210

[51] Int. Cl.$^2$ ........................ B01D 9/04; C07C 29/24; C07C 41/12
[52] U.S. Cl. ............................... 62/532; 55/82; 55/96; 260/615 R; 260/637 R; 261/153
[58] Field of Search ........... 260/637 R, 643 A, 615 R; 62/532; 55/82

[56] References Cited

U.S. PATENT DOCUMENTS

| | | | |
|---|---|---|---|
| 2,186,887 | 1/1940 | Steinbacher | 62/532 |
| 2,252,738 | 8/1941 | Stoerer | 55/82 |
| 2,768,980 | 10/1956 | Pence | 260/637 R |
| 2,787,451 | 4/1957 | Lavery | 261/3 |
| 2,887,851 | 5/1959 | Toulmin, Jr. | 62/532 |
| 3,128,188 | 4/1964 | McIntire | 62/532 |
| 3,148,208 | 9/1964 | Siggel et al. | 260/637 R |
| 3,158,004 | 11/1964 | Klencke | 62/532 |
| 3,349,573 | 10/1967 | Rowekamp | 62/532 |
| 3,824,767 | 7/1974 | Ford | 55/82 |

FOREIGN PATENT DOCUMENTS 698,217 10/1953 United Kingdom ............ 260/643 A

OTHER PUBLICATIONS

Curme, "Glycols", (1952), p. 39.

Primary Examiner—Joseph E. Evans
Attorney, Agent, or Firm—Millen & White

[57] ABSTRACT

Aqueous glycol solutions, used for example, in the deicing of heat exchange surfaces used in defogging systems, are regenerated by freeze crystallization, the ice being separated with relatively little loss of glycol.

20 Claims, 3 Drawing Figures

FREEZE REGENERATION OF GLYCOL SOLUTIONS LOADED WITH WATER

BACKGROUND OF THE INVENTION

This invention relates to a process for the regeneration of glycol solutions loaded with water.

Lower glycols are normally strongly hygroscopic substances, and for this reason mono-, di-, and triethylene glycols have been known for years as desiccants. Thus, these compounds are used, for example, for the drying of gases (U.S. Pat. No. 2,787,451) by introducing the gases at the bottom into a scrubbing tower where they are met by a spray of glycol solution from above. A dried gas is withdrawn from the head of the scrubbing tower in this process. However, glycols are also employed as desiccants for liquids, insofar as these liquids are not miscible with glycol.

Special significance is attributed to the glycols in low-temperature processes where there is the danger of the crystallization of water ice when processing moist liquids or gases, leading to clogging of apparatus parts. In these instances, minor amounts of glycol are added to the gas or to the liquid, before it comes into contact with apparatus parts which are at below 0° C., thereby to prevent a freezing out of water ice.

A typical example for the last-mentioned application is the use in defogging devices (DOS [German Unexamined Laid-Open Application] No. 2,224,671). In these defoggers, utilized for the defogging of airports, freeways, etc., the air is blown by means of a blower over the evaporator and liquefier of a refrigerating machine and, due to the cooling of the air at the evaporator, a condensation or freezing out of the fog is accomplished. Since most of the moisture, in case of outside temperatures of below about +5° C., is precipitated in the form of ice on the evaporator of the refrigerating machine, the heat transfer from the air and/or fog to the evaporator drops rapidly as soon as the ice layer has reached a certain thickness. Therefore, it has been desirable to suppress the deposition of ice on the evaporator at the outset, and for this reason the evaporator is sprinkled, in the conventional process, with an aqueous glycol solution. Since a device as utilized, for example, for airport defogging requires per operating hour about 100–150 kg. of glycol as the antifreeze agent, a regeneration of the glycol must be provided, unless this quantity is to be discarded.

The heretofore customary regenerating method (U.S. Pat. No. 2,787,451) resides in heating the glycol solution and distilling off part of the absorbed water. However, this process has the disadvantage that it requires a large amount of heat energy and cooling water, because large temperature differences must be overcome for the heating and recooling of the solutions. A further disadvantage of the warm regeneration method is that the glycol can be oxidized during heating partially to glycolic acid, which has an extremely corrosive effect on aluminum.

SUMMARY OF THE INVENTION

It is one object of the present invention to provide a process making it possible to again separate the water absorbed by the glycol solution in a manner which is significantly more advantageous from an energy viewpoint.

This object is attained in accordance with the invention by cooling the solution to below its ice point and separating the thus-crystallized ice from the remaining glycol solution.

The regenerating method according to this invention has nowise been obvious, since hydrophilic compounds normally tend toward the formation of mixed crystals with water, and something similar was initially also to be expected from the glycols. However, pure water ice is deposited during the cooling of aqueous glycol solutions, whereby a separation of the components glycol and water becomes feasible.

Furthermore, it had to be expected that the separation of the mother liquor from the ice slurry would become increasingly difficult in proportion to the quantity of frozen-out ice. However, this has likewise proven groundless. Consequently, to conduct the process in accordance with this invention, a one-stage crystallization of the ice is sufficient.

DETAILED DESCRIPTION

Figure 1:
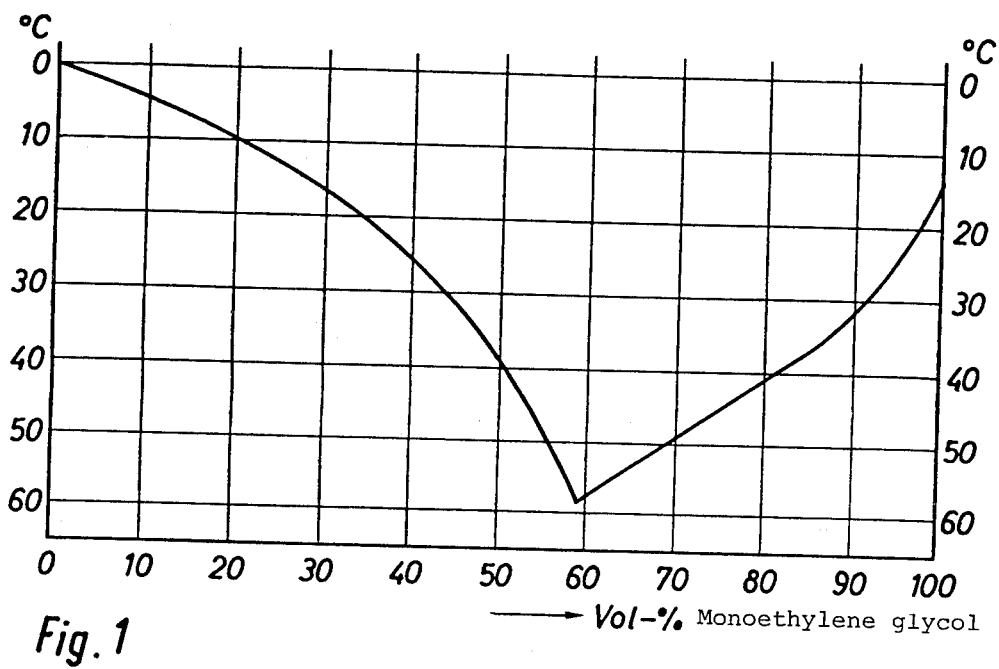
FIG. 1 is a liquid-solid phase diagram of a monoethylene glycol-water mixture.

To conduct the process of this invention, the water-loaded glycol solution must be cooled to below the temperature at which the water ice begins to crystallize (ice point). The dependency of the onset of crystallization on the concentration of a solution of monoethylene glycol and on the temperature can be seen from FIG. 1. In the area underneath the curve, ice is crystallized on the left-hand side of the eutectic point and monoethylene glycol is crystallized on the right-hand side thereof. For example, if a 20% glycol solution, the crystallizing point of which is about −10° C., is subjected to the process of this invention, it is sufficient to cool the solution to −12° to −15° C. to attain shortly thereafter a rapid crystallization of water ice.

Figure 3:
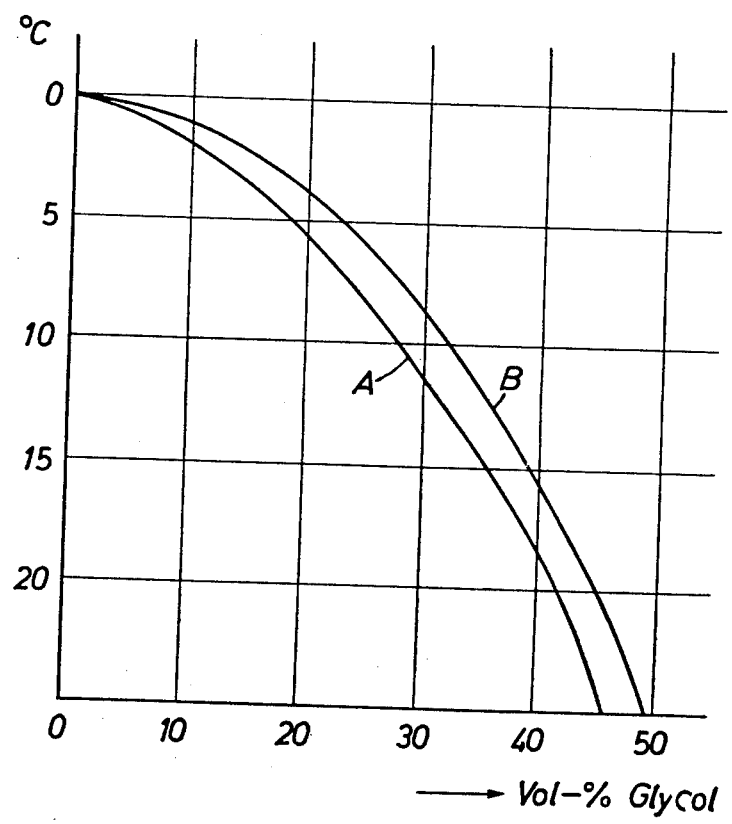
FIG. 3 shows crystallization temperatures for aqueous mixtures of diethylene glycol and triethylene glycol.

FIG. 3 shows the onset of crystallization for diethylene glycol (curve A) and triethylene glycol (curve B) in dependence on the temperature and the glycol content of the solution.

In this connection, it proved to be advantageous to allow the glycol solution to flow through a heat exchanger, the other cross section of this heat exchanger being charged with refrigerant from a refrigerating machine.

The amount of separated ice depends on the temperature to which the glycol solution is cooled. This temperature can, in turn, be controlled by the temperature of the refrigerant and the residence time in the heat exchanger. When cooling a 20% strength monoethylene glycol solution to about −17° C., an increase in the concentration of the solution to about 30% is attained with a sufficiently long residence time of the solution in the heat exchanger. Such a rise in concentration is normally sufficient for technical processes, since the glycol solution is then capable of acting as an antifreeze and of reabsorbing, for example, the amount of water precipitated by crystallization on the cooling surfaces of defoggers.

It has been found that the size of the thus-separated ice crystals increases with the time spent in cooling the solution. In contrast thereto, a subcooling of the solution proved to be very damaging, since in case of subcooled solutions very fine ice crystals are suddenly produced which can be separated from the mother liquor only with difficulties. In accordance with a special embodiment of the present invention, the possibility has thus been provided, in order to avoid subcooling, to recycle a small partial stream of ice-containing mother liquor to the solution to be regenerated, whereby the latter is continuously inoculated.

The crystallized ice can be separated from the mother liquor by centrifuging or filtering. In this connection, continuously operating filter centrifuges and filter presses proved to be especially advantageous.

A decisive factor for the purity of the thus-separated ice and thus for the separating effect attained is the separation of the mother liquor from the crystals. The regenerating effect becomes greater with an increasing completeness of the separation of the mother liquor. Accordingly, other known solid-liquid separation techniques can be used aside from filtration and centrifugation, attention being directed, for example, to class 210 of the U.S. Patent Office Manual of Classification as well as to chemical engineering handbooks, e.g., Perry's, and also the ice recovery techniques in desalination freezing processes.

According to a special embodiment of the idea of this invention, the provision has thus been made to continue the centrifuging or "nutsch operation" with a supply of heat until about 10–20% of the separated ice has been superficially melted off. The heat can be supplied by blowing warm air onto the precipitated ice. With the aid of the resultant water, the mother liquor is flushed out of the crystal slurry to an almost quantitative extent.

A like effect with respect to the precipitated ice is also achieved if the ice is sprayed with a small amount of water (about 20%, based on the ice to be purified) during the centrifuging step; this process has the advantage of a significantly shortened centrifuging period.

The same measures of blowing warm air into the system or spraying water thereon are also advantageous when utilizing filter presses.

The invention will furthermore be explained with reference to the schematically illustrated embodiment.

Figure 2:
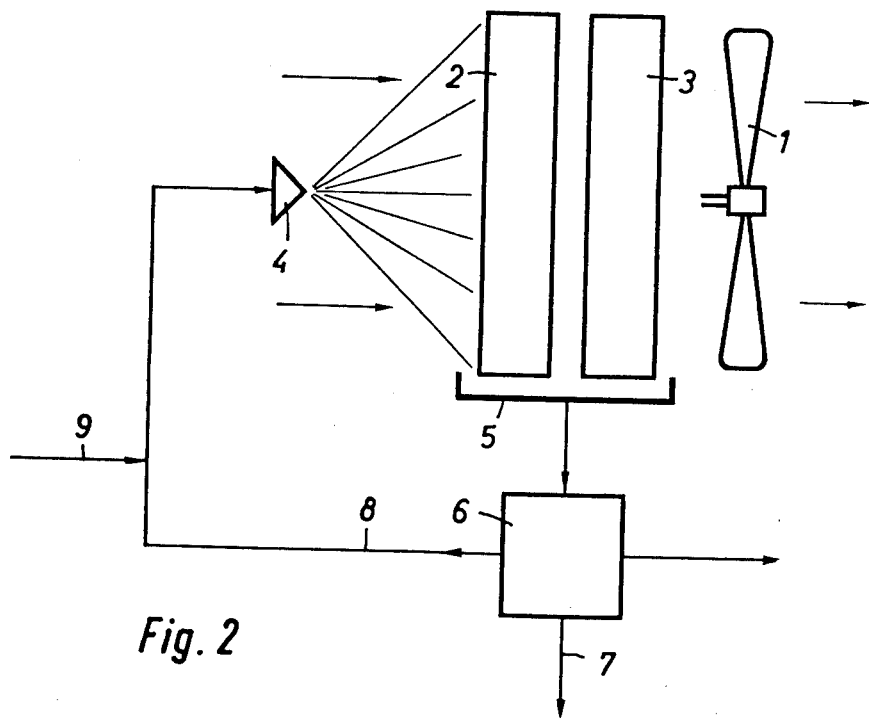
FIG. 2 is a schematic drawing of a defogging system.

FIG. 2 illustrates the essential parts of a defogging device as it can be used, for example, to defog airports. With the aid of a blower 1, foggy air is taken in from the left-hand side via an evaporator 2 of a refrigerating machine and greatly cooled at that point. During this step, the atmospheric humidity is condensed on the evaporator 2. The air then passes furthermore through a mist precipitator 3 and is then forced through the blower 1 toward the right-hand side. Upstream of the evaporator 2, a spray nozzle 4 is disposed making it possible to spray the evaporator 2 with glycol solution to prevent an ice precipitation on the evaporator. The liquid running off from the evaporator 2 and the mist precipitator 3 is collected in a collecting trough 5 and conducted to a regenerating unit 6. In the regenerating unit 6, the glycol solution is subjected to the freezing-out process of this invention, and part of the water contained in the solution is separated in the form of ice. The ice is ejected via conduit 7. A conduit 8 connects the regenerating unit 6 with the spray nozzle 4, which is fed in this way with regenerated glycol. Via a conduit 9, glycol losses can be replenished.

The advantages of the process of this invention will furthermore be demonstrated with the aid of several tables.

Tables 1(a) to 1(c) show comparisons between the regenerating method of this invention and those methods wherein, without the regeneration of the invention, a portion of consumed solution is continuously discharged to prevent the water concentration from becoming too high.

The numerical data stem from a defogger according to FIG. 2. The values in Table 1(a) relate to monoethylene glycol as the solvent, and to an air temperature of −4° C. The saving in glycol is 90%. Table 1(b) represents the values for diethylene glycol (outside temperature −4° C.; saving: 90%), and Table 1(c) shows the values for triethylene glycol (outside temperature −4° C.; saving: 88%).

TABLE 1(a)

|  | Without Regeneration | | With Regeneration | |
| --- | --- | --- | --- | --- |
|  | Quantity l./h. | Glycol Content vol.-% | Quantity l./h. | Glycol Content vol.-% |
| Runoff from cooler 2 and mist precipitator 3 | 3455 | 21.0 | 3455 | 21.0 |
| Discharge from 6 | 576 | 21.0 | 466 | 2.5 |
| Reflux to the spray nozzle 4 | 2879 | 21.0 | 2989 | 23.8 |
| Glycol feed 9 | 121 | 100.0 | 11 | 100.0 |
| Sprayed solution | 3000 | 24.2 | 3000 | 24.2 |

TABLE 1(b)

|  | Without Regeneration | | With Regeneration | |
| --- | --- | --- | --- | --- |
|  | Quantity l./h. | Glycol Content vol.-% | Quantity l./h. | Glycol Content vol.-% |
| Runoff from cooler 2 and mist precipitator 3 | 3315 | 27.5 | 3315 | 27.5 |
| Discharge from 6 | 625 | 27.5 | 472 | 4 |
| Reflux to the spray nozzle 4 | 2690 | 27.5 | 2840 | 31.6 |
| Glycol feed 9 | 175 | 100 | 17 | 100 |
| Sprayed solution | 2855 | 32.0 | 2855 | 32.0 |

TABLE 1(c)

|  | Without Regeneration | | With Regeneration | |
| --- | --- | --- | --- | --- |
|  | Quantity l./h. | Glycol Content vol.-% | Quantity l./h. | Glycol Content vol.-% |
| Runoff from cooler 2 and mist precipitator 3 | 3280 | 32.5 | 3280 | 32.5 |
| Discharge from 6 | 665 | 32.5 | 480 | 5.5 |
| Reflux to the spray nozzle 4 | 2615 | 32.5 | 2798 | 37.2 |
| Glycol feed 9 | 218 | 100 | 26 | 100 |
| Sprayed solution | 2825 | 37.8 | 2825 | 37.8 |

Table 2 shows the dependence of the separating effect on the centrifuging time. The measurements were conducted with a 20% by volume monoethylene glycol solution which was cooled to −11.5° C. ± 0.5° C. As can be seen from Table 2, the optimum centrifuging time ranges between 1 and 5 minutes. With a shorter centrifuging period, the amount of centrifuged mother liquor is still to small, whereas with a longer duration of the centrifuging step, the effect of the melting of the ice becomes noticeable. The centrifuge had a diameter of 17 cm and was operated at 900 rpm.

TABLE 2

| Centrifuging Period min. | Glycol Content of Centrifuged Matter vol.-% | Glycol Content of Separated Ice vol.-% | Separated Amount of Ice Based on Initial Solution vol.-% |
|---|---|---|---|
| 0.3 | 22.5 | 4.0 | 10 |
| 1 | 24.0 | 3.7 | 16 |
| 5 | 23.9 | 2.6 | 15.5 |
| 10 | 22.5 | 1.0 | 9.5 |
| 20 | 20.0 | 0.2 | 2.0 |

Table 3 shows the dependency of the separating effect on the concentration of the glycol solutions utilized when the water is being frozen out. In the measurements on which Table 3 is based, the monoethylene glycol solution was cooled with a brine, the temperature of which was 6°-8° C. below the ice point of the respective solution. The centrifuging time was about 6.5 minutes. The reduction of the separated amount of ice with growing glycol content of the initial solution is related to the stronger inclination of the curve in FIG. 1 at higher glycol contents.

TABLE 3

| Glycol Content of Initial Solution vol.-% | Temperature of Centrifuged Product = Final Cooling Temperature °C. | Ice Point of Initial Solution °C. | Glycol Content of Centrifuged Product vol.-% | Glycol Content of Separated Ice vol.-% | Separated Amount of Ice Based on Initial Solution vol.-% |
|---|---|---|---|---|---|
| 5 | −4.5 | −2.0 | 7.5 | 1.0 | 35 |
| 10 | −6.0 | −4.0 | 13.8 | 1.8 | 29 |
| 15 | −9.0 | −7.0 | 21.0 | 2.4 | 24.5 |
| 20 | −11.5 | −9.5 | 24.5 | 2.5 | 19.0 |
| 25 | −15 | −12.5 | 28.2 | 3.0 | 14.5 |
| 30 | −19 | −16.5 | 34.0 | 3.0 | 11.0 |

Table 4 shows the scrubbing effect of ice water on the purity of the separated ice. These values are based on laboratory experiments, wherein the steps were carried out respectively with 500 ml. of solution with 25 vol.-% of monoethylene glycol. In Experiment 1, the centrifuging time was 1 minute, and in Experiment 2, this time was 6.5 minutes. No water was sprayed on. In Experiments 3 and 4, the centrifuging was conducted for respectively 1 minute, then water was sprayed on, and then another minute of centrifuging was carried out. It can be seen that the glycol content of the separated ice decreases at a comparable centrifuging time and, on the other hand, a great saving in centrifuging time can be obtained by the spraying on of water.

TABLE 4

| Centrifuging Time min. | Amount of Water Sprayed on ml. | Glycol Content of Centrifuged Product I vol.-% | Glycol Content of Centrifuged Product II vol.-% | Glycol Content of Separated Ice vol.-% |
|---|---|---|---|---|
| 1 | — | 27.8 | — | 5.5 |
| 6.5 | — | 28.2 | — | 3.0 |
| 1+1 | 10 | 30 | 23.6 (10 ml.) | 4.5 |
| 1+1 | 20 | 31 | 22.4 (21 ml.) | 3.0 |

The regeneration of glycol solutions by freezing in accordance with this invention is, however, also markedly superior to the conventional glycol warm regeneration. During the warm regeneration, the glycol solution must be heated by about 100° C. Besides, the heat of evaporation of the water must be provided which amounts to about 536 kcal/kg. of water. However, in the process of this invention, a cooling of the loaded glycol solution by 5°-10° C. is sufficient, and one must only provide the melting heat of the ice, which amounts to 80 kcal/kg.

The process can be performed with mono-, di- or triethylene glycol. Monoethylene glycol is preferred because of its higher freezing point depression and lower viscosity and because the quantity by weight that is necessary for the process is smallest in the case of monoethylene glycol.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the regeneration of glycol solutions loaded with water, wherein the solution is cooled to below its ice point without deleterious subcooling to form a crystal slurry, and the thus-crystallized ice is separated from the remaining glycol solution.

2. A process according to claim 1, wherein the ice is separated from the glycol solution by centrifuging.

3. A process according to claim 2, wherein the ice is sprayed with water during the centrifuging step.

4. A process according to claim 2, wherein the ice is quickly superficially warmed during centrifuging.

5. A process according to claim 1, wherein the ice is separated from the glycol solution by filtering.

6. A process according to claim 5, wherein the ice is sprayed with water during filtering.

7. A process according to claim 5, wherein the ice is quickly superficially warmed during filtering.

8. A process according to claim 1, wherein to avoid said deleterious subcooling, the solution to be regenerated is continuously innoculated with a partial stream of ice-containing solution to initiate crystallization.

9. In a defogging process comprising passing fog over cold heat exchange surfaces to condense out water thereon, washing said heat exchange surfaces with a glycol-water mixture to remove the ice and load the mixture with additional water, and regenerating resultant loaded glycol-water mixture,
   wherein the improvement comprises regenerating in accordance with the process of claim 1.

10. A process according to claim 9 wherein the glycol is mono-, di- or tri-ethylene glycol.

11. A process according to claim 9, wherein the glycol is monoethylene glycol.

12. A process according to claim 9, wherein the ice is separated from the mother liquor by centrifuging or filtering and the ice is superficially melted during said separating to form sufficient water to flush out mother liquor from the crystal slurry to almost a quantitative extent.

13. A process according to claim 12, wherein the separating is conducted by centrifuging and about 10-20% of the separated ice is superficially melted.

14. A process according to claim 9, wherein to avoid said deleterious subcooling, the solution to be regenerated is continuously innoculated with a partial stream of ice-containing solution to initiate crystallization.

15. A process according to claim 13, wherein to regenerated is continuously innoculated with a partial stream of ice-containing solution to initiate crystallization.

16. A process according to claim 4, wherein about 10–20% of the separated ice is melted to form sufficient water to flush out mother liquor from the crystal slurry to almost a quantitative extent.

17. A process according to claim 1, wherein the loaded glycol solution is cooled by 5°–10° C.

18. A process according to claim 9, wherein the loaded glycol solution is cooled by 5°–10° C.

19. A process according to claim 1, wherein the solution is cooled by a fluid medium having a temperature of 6°–8° C. below the ice point of said solution.

20. A process according to claim 9, wherein the solution is cooled by a fluid medium having a temperature of 6°–8° C. below the ice point of said solution.

* * * * *

UNITED STATES PATENT AND TRADEMARK OFFICE
CERTIFICATE OF CORRECTION

PATENT NO. : 4,081,257
DATED : MARCH 28, 1978
INVENTOR(S) : EBERHARD LASSMANN ET AL.

It is certified that error appears in the above-identified patent and that said Letters Patent are hereby corrected as shown below:

Claim 15, line 4: Change "wherein to regenerated" to read
-- wherein to avoid said deleterious subcooling, the solution to be regenerated --.

Signed and Sealed this

Twenty-sixth Day of September 1978

[SEAL]

Attest:

RUTH C. MASON
Attesting Officer

DONALD W. BANNER
Commissioner of Patents and Trademarks